United States Patent [19]

Alexander

[11] Patent Number: 4,916,230

[45] Date of Patent: Apr. 10, 1990

[54] PROCESS FOR PREPARING NOVEL N-(ACYLOXY-ALKOXY)CARBONYL DERIVATIVES USEFUL AS BIOREVERSIBLE PRODRUG MOIETIES FOR PRIMARY AND SECONDARY AMINE FUNCTIONS IN DRUGS

[75] Inventor: Jose Alexander, Lawrence, Kans.

[73] Assignee: Merck & Co., Inc., Rahway, N.J.

[21] Appl. No.: 627,156

[22] Filed: Jul. 2, 1984

[51] Int. Cl.$^4$ .................. C07D 211/78; C07D 211/90
[52] U.S. Cl. .................................... 546/318; 260/404; 260/408; 546/227; 548/531; 548/535; 558/270; 558/271; 558/272

[58] Field of Search ............... 558/270, 271, 272, 273; 260/404, 408; 546/318, 227; 548/531, 535

[56]  References Cited

U.S. PATENT DOCUMENTS 3,655,717  4/1972  Becher et al. ...................... 558/272
4,377,590  3/1983  Myers ................................ 514/193

Primary Examiner—Werren B. Lone
Attorney, Agent, or Firm—Manfred Polk; Joseph F. DiPrima

[57]  ABSTRACT

This invention relates to a new one-step process for preparation of novel N-(acyloxyalkoxy)carbonyl derivatives useful as bioreversible prodrug moieties for drugs having a primary or secondary amine function thereon.

10 Claims, No Drawings

PROCESS FOR PREPARING NOVEL N-(ACYLOXY-ALKOXY)CARBONYL DERIVATIVES USEFUL AS BIOREVERSIBLE PRODRUG MOIETIES FOR PRIMARY AND SECONDARY AMINE FUNCTIONS IN DRUGS

BACKGROUND OF THE INVENTION

This invention relates to a new one-step process for preparation of novel N-(acyloxyalkoxy)carbonyl derivatives useful as bioreversible prodrug moieties for primary and secondary amine functions in drugs.

For compounds which ionize, the rate of transport through biomembranes appear to be proportional to the concentration of undissociated molecules and the lipid solubility. It is often advantageous to perform derivatization of polar groups to aid absorption, since this would make the compounds more hydrophobic and hence more lipid soluble. Carbamylation confers such properties to amines since carbamates do not ionize. However, success with carbamate ester latentiation requires that it must be hydrolyzed to carbamic acid and an alcohol moiety after penetration through the biological barrier. This is especially true of carbamates of secondary amines, the rates of in vitro hydrolysis of which are $10^5$–$10^9$ times slower than that of the corresponding primary amines. In this regard, there does not appear to be a carbamate ester specific hydrolytic enzyme in mammals. Though cholinesterases hydrolyze carbamates and become reversibly inhibited in the process, the rates are too slow for practical use. Hence, modified carbamates with an enzymically hydrolyzable ester function were designed as prodrugs for amines. Esterase catalysed hydrolysis of the ester moiety triggers the regeneration of the parent amine from such derivates as depicted below.

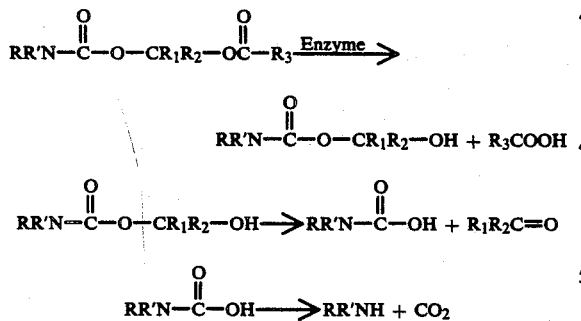

wherein RR'N, $R_1$, $R_2$ and $R_3$ are as defined further along.

For the purposes of this specification, the term "prodrug" denotes a derivative of a known and proven primary or secondary amino functional drug (e.g. timolol, methyldopa, thiabendazole, etc.) which derivative, when administered to a warm-blooded animal, "cleaves" in such a manner as to release the proven drug form at its target site or sites of activity. The enzymatic and/or chemical hydrolytic "cleavage" of the compounds of the instant invention occurs in a manner such that the proven drug form is released while the remaining "cleaved" moiety remains nontoxic and is matabolized in such a manner that nontoxic, metabolic products are produced.

DESCRIPTION OF THE PRIOR ART

U.S. patent application. Ser. No. 507,316 (1983) discloses compounds and methods of preparing the same which fall within the above-described generic formula. A review of the previously stated patent readily shows that the method of making such structures is a two-step process, viz. treating a primary or secondary amine with an α-haloalkyl haloformate to give an α-haloalkyl carbamate followed by displacement of the halogen with an acyloxy group by treatment with a metal salt of the carboxylic acid; the metal used could be alkali, alkaline earth, or silver, mercury, and the like.

But there are instances where the application of the method could result in poor yields as a result of side reactions. For example, silver salts could interact with a free thiol function or mercury salts could give rise to mercuration of highly activated aromatic rings and double bonds. So there exists a need for making N-(acyloxyalkoxy)carbonyl derivatives more conveniently and with better selectivity.

SUMMARY OF THE INVENTION

In accordance with this invention, there is provided a new process for the preparation of the novel N-(acyloxyalkoxy)carbonyl derivatives of the formula:

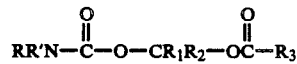

wherein RR'N represents a primary or secondary amine drug and $R_1$, $R_2$ and $R_3$ are as defined below, making use of a novel reagent of the following formula (I) below:

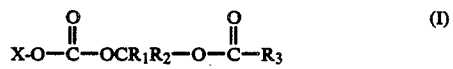

wherein
X is
(a) phenyl substituted with one or more of the substituents selected from the group consisting of nitro, halo (fluoro, chloro, etc.), cyano, and the like; alkylsulfonyl wherein the alkyl moiety has from 1-6 carbon atoms such as methyl, ethyl, propyl, pentyl, and the like; alkylsulfenyl wherein the alkyl moiety has from 1-6 carbon atoms such as methyl, ethyl, propyl, pentyl and the like; trihalomethyl, trihalomethylthio, trihalomethylsulfonyl, trihalomethylsulfenyl or
(b) a radical selected from the group consisting of $C_{1-5}$ polyhaloalkyl such as trifluoroethyl, trichloroethyl and the like and $C_{2-12}$ alkylsulfonylalkyl such as methylsulfonylmethyl, ethylsulfonylpropyl, propylsulfonylmethyl and methylsulfonylbutyl and the like;

$R_1$ and $R_2$ can be the same or different radical and are selected from the group consisting of hydrogen or alkyl having from 1 to 6 carbon atoms such as methyl, ethyl, propyl, butyl, pentyl, and the like; substituted $C_{1-5}$ alkoxycarbonyl alkyl wherein the alkoxy group has from 1 to 5 carbon atoms such as methyl, propyl, pentyl, and the like; aryl such as phenyl and aralkyl such as benzyl.

$R_3$ is alkyl having from 1 to 20 carbon atoms such as methyl, ethyl, hexyl, hexadecyl and the like; alkenyl having from 2 to 20 carbon atoms such as allyl, butenyl, octenyl, decenyl, hexadecenyl, and the like; alkynyl having from 2 to 5 carbon atoms such as propargyl; aryl such as phenyl, α-naphthyl, β-naphthyl, and the like; aralkyl having from 7 to 10 carbon atoms such as benzyl, tolyl, and the like; cycloalkyl having from 3 to 8 carbon atoms such as cyclohexyl, cyclopentyl, cyclooctyl, and the like; cycloalkenyl having from 3 to 10 carbon atoms such as cyclohexenyl, cyclopropenyl, cyclodecenyl, and the like; carboxyalkyl wherein the alkyl group has from 2 to 20 carbon atoms such as succinyl, glutaryl, and the like; carboxy cycloalkyl wherein the cycloalkyl group has from 5 to 20 carbon atoms such as carboxycyclohexyl, carboxycyclopentyl, carboxycyclodecyl, carboxycycloheptadecyl; haloalkyl wherein the alkyl portion has from 2 to 20 carbons such as ethyl, pentyl, heptyl, octyl, decyl, hexadecyl, and the like; and halo is chloro, bromo, iodo or fluoro; chlorohexyl, chloropentyl, and the like; alkoxy carbonylalkyl wherein the alkyl moiety has from 2 to 10 carbon atoms such as methoxycarbonylmethyl, butoxycarbonylethyl, methoxycarbonylhexyl, and the like; and the alkoxy portion is $C_{1-5}$ such as carbethoxy hexyl and the like; alkylsulfoxide wherein the alkyl group has from 2 to 20 carbon atoms such as ethyl sulfinyl propyl and the like; carbamyl substituted alkyl or aralkyl having from 2 to 20 carbon atoms such as hexylcarboxamide and the like; saturated or unsaturated mono- or poly-heterocyclics having from 1 to 3 rings and having one or more of nitrogen, sulfur or oxygen atoms in the rings such as furyl, morpholinyl, oxazolidinyl, pyridyl, piperidinyl, pyrolidinyl, pyrolyl, 1,2,5-thiazolyl and the like.

Accordingly, it is an object of this invention to provide novel (cyloxyalkoxy)carbonate derivatives which are useful as starting materials for novel one-step synthesis of bioreversible prodrug moieties for drugs or medicaments having primary or secondary amine functions thereon which when administered to warm-blooded animals are characterized as being more readily bioavailable, less irritating to topical and gastric mucosal membranes and more permeable through topical membranes, e.g., ophthalmic membrane or skin, than are the parent drugs from which they are derived.

A further object of this invention is to provide such prodrug form of conventional primary and secondary amine compounds which, following administration, will "cleave" in such a manner as to enable the original parent moiety to be released at its therapeutic site or sites of activity and to further permit the cleaved moiety, unassociated with the parent moiety, to be metabolized in a nontoxic fashion.

Another object of this invention is to provide prodrugs of medicaments or drugs having primary or secondary amine functions thereon to provide increased biomembrane transport such that the drug is more bioavailable from the GI tract, the rectum, the skin and the eye of the human body.

A further object of this invention is to provide prodrug compounds which utilize hydrolytic enzymes to generate the parent amine-type drug from the prodrug or carbamate protecting group.

A still further object of this invention is to provide prodrugs of amines wherein the ester function is remote from the carbamate carbonyl and thus through enzymatic hydrolysis lead to the generation of carbamic acid which will undergo fast decarboxylation releasing the amine parent drug.

These and other objects and advantages of the present invention will become apparent from the following description.

DETAILED DESCRIPTION OF THE INVENTION

The invention concerns preparation and use of novel (acyloxyalkyl)carbonate derivatives that are used as a starting material in a novel one-step synthesis of bioreversible prodrug moieties for drugs or medicaments having primary or secondary amine functions which increases the bioavailability of said prodrug or medicament in the gastrointestinal tract, rectum, skin and eye of the patient (animal and human). The novel (acyloxyalkyl)carbonate derivatives of the invention are represented by the following formula:

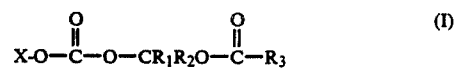

wherein X, $R_1$, $R_2$ and $R_3$ are as previously defined and may be prepared by the general reaction sequences below:

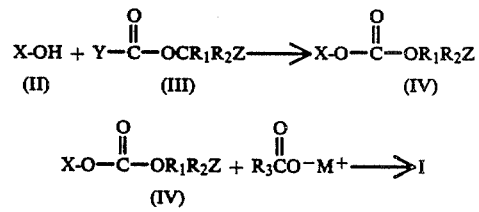

The method for preparing compound of the formula (I) consists of reacting the hydroxy (phenolic) compound X—OH (II) with a haloformate of formula (III) where Y is chloro, bromo or iodo, or an amine conjugate such as pyridinium or imidazolium and Z is chloro, bromo or iodo. This reaction is carried out in nonprotic halogenated solvents such as chloroform, dichloromethane and the like or in solvents such as ethyl ether, tetrahydrofuran, dioxane, dimethoxyethane, ethyl acetate, acetonitrile and the like. The reaction can be carried out at temperatures from −78° C. to 100° C., preferably at 0° C. to room temperature in the presence of a base such as pyridine, triethylamine, 1,8-bis(dimethylamino)naphthalene, N-methylmorpholine and 4-dimethylaminopyridine and the like.

The Z moiety of the resulting compound (IV) is displaced with an acyl group in the presence of a reactant such as an alkali or alkaline earth salt of a carboxylic acid or a metal salt of carboxylic acid. The metal ion M is selected from an alkali or alkaline earth metal such as sodium, potassium, magnesium, calcium, or can be a metal selected from silver, mercury, zinc and the like. The displacement reaction can be carried out in a solvent which is inert to the reactant such as alcohol, water, dimethylformamide, hexamethylphosphoramide, acetonitrile, benzene, toluene, xylene, or an organic acid $R_3CO_2H$ such as acetic acid, propionic acid, and the like. This step of the reaction is carried out between ambient or room temperature to the boiling point (reflux) of the particular solvent employed, preferably between 25° C. to 150° C.

The final product (I) is isolated from the reaction mixture by methods known in the art such as filtration or extraction into a solvent followed by evaporation of the solvent.

The novel (acyloxyalkyl)carbonate derivatives of the present invention are employed as a starting material in the novel one-step method of preparing compounds disclosed in the prior art [U.S. Ser. No. 507,316 (1983)]. The patent discloses N-(acyloxyalkoxy)carbonyl derivatives of primary and secondary amine drugs of the formula:

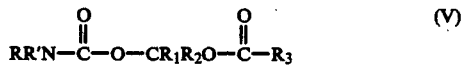

$$RR'N-\overset{O}{\underset{\|}{C}}-O-CR_1R_2O-\overset{O}{\underset{\|}{C}}-R_3 \quad (V)$$

wherein RR'N represents a primary or secondary amine drug and, $R_1$, $R_2$ and $R_3$ are as previously defined. The present invention discloses a novel reaction of RR'NH with the novel reagent of formula (I) below:

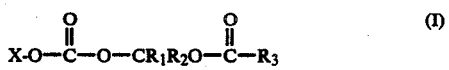

$$X-O-\overset{O}{\underset{\|}{C}}-O-CR_1R_2O-\overset{O}{\underset{\|}{C}}-R_3 \quad (I)$$

in the presence of a polar aprotic solvent such as dimethylformamide, dimethylacetamide, hexamethylphosphorictriamide, 1,3-dimethyl-2-imidazolidinone and optionally a catalyst such as 1-hydroxybenzotriazole, imidazole, pyrazole, 1,2,4-triazole and the like at temperatures ranging from 0° to 100° C., preferably at 25° to 60° C. to obtain the compounds of formula (V).

RR'N can represent any drug, pharmaceutical or medicament having a primary or secondary amine function thereon. Typical drugs, pharmaceuticals or medicaments that can be used and have a primary or secondary amine function thereon are timolol, norfloxacin, dimethoxyphenethylamine, propranolol, atenolol, pindolol, betaxalol and methyldopa.

Various active agents provide beneficial effects when administered to patients. Representative drugs, pharmaceuticals or medicaments which can be used and which contain primary or secondary amine functions thereon are listed below. One skilled in the art will realize that the list below is not exclusive and the invention is applicable to other primary and secondary amino functional drugs as well.

(a) Those drugs, pharmaceuticals or medicaments similar to timolol: acebutalol, albuterol, alprenolol, atenolol, bucindolol, bunolol, butopamine, butoxamine, carbuterol, carteolol, colterol, deterenol, dexpropranolol, diacetolol, dobutamine, exaprolol, fenoterol, fenyripol, labotolol, levobunolol, metolol, metaproterenol, metoprolol, nadolol, exprenolol, pamatolol, penbutalol, pindolol, pirbuterol, practolol, prenalterol, primidolol, prizidilol, procaterol, propranolol, quinterenol, rimiterol, ritodrine, sotolol, soterenol, sulfinolol, sulfonterol, suloctidil, tazolol, terbutaline, tiprenolol, tipropidil, tolamolol, etc.

(b) Structurally similar to thiabendazole: albendazole, albutoin, alinidine, alizapride, amiloride, aminorex, aprinocid, cambendazole, cimetidine, clonidine, cyclobendazole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, etc.

(c) Structurally similar to dimethoxyphenethylamine: adrenelone, aletamine, amidephrine, amphetamine, aspartame, bamethan, betahistine, clorprenaline, chlortermine, dopamine, etryptamine, fenfluramine, norepinephrine, tocainide, etc.

Other drugs are acyclovir, enviroxime, etoprine, nifedipine, nimodipine, triamterene, vidarabine, methyldopa, epinephrine and those structurally similar to norfloxacin such as pipemidic acid, 1-ethyl-6-fluoro-1,4-dihydro-4-oxo-7-(1-piperazinyl)-1,8-naphthyridine-3-carboxylic acid and 1-cyclopropyl-6-fluoro-1,4-dihydro-4-oxo-7-(1-piperezinyl)-3-quinolinecarboxylic acid.

The prodrug compounds of Formula (V) of the invention can be used to treat any condition for which the parent drug, medicament or pharmaceutical is useful. For example, if timolol is the parent drug of choice, the prodrug can be used for any condition or treatment for which timolol would be administered.

Thus, the prodrug compounds of Formula (V) may be administered orally, topically, parentally, by inhalation spray or rectally in dosage unit formulations containing conventional, non-toxic pharmaceutically acceptable carriers, adjuvants and vehicles.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectibles.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

For topical use, creams, ointments, jellies, solutions, suspensions or the like containing the prodrugs are employed according to methods recognized in the art.

Naturally, the therapeutic dosage range for the compounds of the invention will vary with the size and needs of the patient and the particular pain or disease symptom being treated. However, generally speaking, the following dosage guidelines will suffice. Orally, the therapeutic dose required for a compound of the invention will generally, on a molecular basis, mimic that for the parent primary or secondary amine drug. On a topical basis, application of a 0.01% to 2.5% concentration of a compound of the invention (in a suitable topical carrier material) to the affected site should suffice.

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Other dosage forms such as ophthalmic dosage forms contain less active ingredient such as for example from 0.1 mg to 5 mg. Dosage unit forms will generally contain between from about 0.1 mg to about 1 g of active ingredient.

It will be understood, however, that the specific dose level for any particular patient will depend upon a variety of factors including the activity of the specific compound employed, the age, body weight, general heath, sex, diet, time of administration, route of administration, rate of excretion, drug combination and the severity of the particular disease undergoing therapy.

EXAMPLE 1

α-Acetoxyethyl p-nitrophenyl carbonate

To an ice cold reaction mixture of 1.39 g (10 mmol) of p-nitrophenol and 0.8 g (10 mmol) of pyridine in 50 ml chloroform, 1.7 g (1 mmol) of α-chloroethyl chloroformate was added. The cooling bath was removed after half hour and the reaction mixture was stirred at room temperature for 16 hours. After washing successively with water, 0.5% aqueous sodium hydroxide and water, the chloroform layer was dried ($Na_2SO_4$) and evaporated to a thick light yellow oil 2.3 g (93%) which was practically pure α-chloroethyl p-nitrophenyl carbonate. IR (film) 1778 (C=O) cm$^{-1}$. $^1$H NMR ($CDCl_3$) 1.93 (d, 3H, CHMe), 6.53 (q, 1H, CHCl), 7.40 (d, 2H, aromatic), 8.26 (d, 2H, aromatic).

To a solution of 1 g (4 mmol) of the above chloroethyl carbonate in 25 ml of acetic acid, 1.5 g (4.7 mmol) of mercuric acetate was added and stirred at room temperature for 22 hours. The acetic acid was evaporated off in vacuum at room temperature and the residue taken in ether was washed free of acid. Evaporation of ether gave 1.1 g of a thick oil. Chromatography of this on silica gel using chloroform-ethyl acetate (95:5) gave 0.82 g (74.5%) of the pure α-acetoxyethyl p-nitrophenyl carbonate. IR (film) 1745 (C=O), 1616, 1594, 1527, 1492, 1349, 1266, 1214, 1109, 1076, 858 cm$^{-1}$. $^1$H NMR ($CDCl_3$) 1.62 (d, 3H, CHMe), 2.13 (s, 3H, OAc), 6.86 (q, 1H, CHOAc), 7.41 (d, 2H, aromatic), 8.28 (d, 2H, aromatic).

EXAMPLE 2

Acetoxymethyl p-nitrophenyl carbonate

This compound was prepared using the same procedure as above, but using chloromethyl chloroformate instead of α-chloroethyl chloroformate. It has the following spectral properties. IR (film) 1746 cm$^{-1}$ (C=O), NMR (CDCl$_3$) 2.18 (s, 3H, OAc), 6.05 (2H, s, CH$_2$), 7.40 (d, 2H, aromatic) and 8.27 (d, 2H, aromatic).

EXAMPLE 3

Iodomethyl p-nitrophenyl carbonate

A solution of 1.5 g of p-nitrophenyl chloromethyl carbonate in 100 ml of acetone was refluxed with 5 g of sodium iodide for 5 hours. The acetone was evaporated off. The residue taken in ether was washed successively with water, aqueous sodium bisulfite and water. After drying over sodium sulfate, the ether layer was evaporated to a light yellow oil weighing 1.75 g which was the pure iodomethyl carbonate. IR (film) 1777, 1522, 1202, 953, 867 cm$^{-1}$ NMR (CDCl$_3$) 6.03 (s, 2H, CH$_2$), 7.36 (d, J=10 Hz, 2H, aromatic) and 8.26 (d, J=10 Hz, 2H, aromatic).

EXAMPLE 4

Hexanoyloxymethyl p-nitrophenyl carbonate

A solution of 0.25 g of iodomethyl p-nitrophenyl carbonate and 0.5 g hexanoic acid was heated to reflux in benzene with 0.5 g of silver hexanoate. After two hours the reaction mixture was filtered, and the filtrate was washed successively with aqueous sodium bicarbonate and water. After drying over sodium sulfate, the solvent was evaporated to furnish hexanoyloxymethyl p-nitrophenyl carbonate as a light yellow liquid (0.28 g). IR (film) 1775 (C=O). NMR (CDCl$_3$) 0.9 (t, 3H, J=7 Hz, Me), 1.1–2.0 (m, 6H, (CH$_2$)$_3$), 2.41 (t, 2H, J=7 Hz, COCH$_2$), 5.88 (s, 2H, OCH$_2$O), 7.38 (d, 2H, J=10 Hz, aromatic), 8.21 (d, J=10 Hz, 2H, aromatic).

EXAMPLE 5

Nicotinyloxymethyl p-nitrophenyl carbonate

A mixture of p-nitromethyl iodomethyl carbonate (1.75 g) and silver nicotinate (2.5 g) was refluxed in benzene (50 ml) for 2 ½ hours. The reaction mixture was cooled and filtered. The filtrate was evaporated to yield 1.47 g of a glassy light yellow oil. It was purified by chromatography on silica gel. The pure nicotinyloxymethyl p-nitrophenyl carbonate was eluted with ethyl acetatechloroform (1:4). IR (film) 1780, 1747, 1591, 1525, 1350, 1284, 1224, 864, 740 cm$^{-1}$ NMR (CDCl$_3$) 6.16 (s, 2H, OCH$_2$O), 7.3–7.6 (m, 3H, aromatic), 8.1–8.4 (m, 3H, aromatic), 8.83 (dd, J=5 and 2 Hz, 1H, aromatic) and 9.28 (d, J=2 Hz, 1H, aromatic). MS, m/e 318 (M+), 244, 166, 136, 122, 106, 78.

EXAMPLE 6

4-[2-Hydroxy-3-[N-(1'-acetoxyethoxycarbonyl)isopropylamino]propoxy]indole

A solution of 1 g (4 mmol) of pindolol and 1 g (4 mmol) of α-acetoxyethyl p-nitrophenyl carbonate in 5 ml of dry hexamethylphosphoramide was stirred at room temperature. When the reaction was practically complete (TLC) the reaction mixture was diluted with water to about 100 ml and extracted with ether. The ether extract was washed repeatedly with 0.5% aqueous sodium hydroxide and water, dried (Na$_2$SO$_4$) and evaporated to furnish a residue weighing 1.15 g. Chromatography on silica gel using ethyl acetatechloroform (5:95) for elution gave 0.8 g (52.6%) of the pure acetoxyethyl carbamate as a glass. IR (KBr) 3410, 1745, 1701 cm$^{-1}$. $^1$H NMR (CDCl$_3$) 1.20 and 1.25 (d, 3H each, isopropyl), 1.51 (d, 3H, CHMe), 2.05 (s, 3H, OAc), 3.5 (d, br, 2H, NCH$_2$), 4.13 (m, 4H, HCOH, CHN and OCH$_2$), 6.55 (m, 2H, aromatic), 6.81 (q, 1H, MeCH), 7.0 (m, 3H, aromatic), 8.31 (broad, 1H, aromatic NH). MS, m/e 378 (M+), 275, 202. (M+) calcd. for C$_{19}$H$_{26}$N$_2$O$_6$ 378.1890, obsd. 378.1794.

EXAMPLE 7

[N-(1'-Acetoxyethoxycarbonyl)isopropylamino]-3-(1-naphthyloxy)-2-propanol

The title compound was obtained after column chromatographic purification in 61% yield by the above method using 1.5 g (5 mmol) of propranolol hydrochloride and 1.36 g (5 mmol) of acetoxyethyl p-nitrophenyl carbonate and 1.08 g of proton sponge ®. IR (film) 3475, 1748, 1705 cm$^{-1}$. $^1$H NMR (CDCl$_3$) 1.20 and 1.24 (d, 3H each, CHMe$_2$), 1.49 (d, 3H, CHMe), 2.05 (s, 3H, OAc), 3.51 (d, 2H, NCH$_2$), 3.9–4.5 (m, 4H, HCOH, CHN and OCH$_2$), 6.80 (q, 1H, MeCH), 6.6–8.3 (m, 7H, aromatic). MS, m/e 389 (M+), 286, 202.

EXAMPLE 8

4-[2-Hydroxy-3-[N-(1'-acetoxyethoxycarbonyl)isopropylamino]propoxy]benzeneacetamide The title compound was obtained in 32% yield after chromatographic purification, by the above method from atenolol. IR (film) 3476, 1747, 1700, 1682 cm$^{-1}$. $^1$H NMR (CDCl$_3$) 1.21 (d, 6H, CHMe$_2$), 1.48 (d, 3H, CHMe), 2.03 (s, 3H, OAc), 3.40 (d, 2H, NCH$_2$), 3.46 (s, 2H, NCOCH$_2$), 3.8–4.3 (m, 5H, OCH$_2$, OH, HCO and NCH), 5.7 and 6.16 (s, br, 1H each CONH$_2$), 6.8 (q, 1H, MeCH), 6.83 (d, 2H, aromatic), 7.13 (d, 2H, aromatic).

EXAMPLE 9

3-[3-Acetoxymethoxycarbonyl-t-butylamino-2-hydroxypropoxy]-4-morpholino-1,2,5-thiadiazole The title compound prepared by the above method using timolol and acetoxymethyl p-nitrophenyl carbonate has the following spectral properties. IR (film) 3480, 1763, 1726 cm$^{-1}$. $^1$H NMR (CDCl$_3$) 1.43 (s, 9H, C(Me)$_3$), 2.08 (s, 3H, OAc), 3.6–3.8 (m, 10H, morpholino H and NCH$_2$), 4.2 (m, 1H, HCO), 4.43 (d, 2H, OCH$_2$), 5.73 (s, 2H, OCH$_2$O). MS, m/e 432 (M+),433 (M+1)+, 377, 287, 246.

Anal. calcd. for C$_{17}$H$_{28}$N$_4$O$_7$S: C, 47.21; H, 6.52; N, 12.95. Found: C, 46.83; H, 6.59; N, 12.58.

EXAMPLE 10

1-[N-(1'-Acetoxyethoxycarbonyl)isopropylamino]-3-[p(cyclopropyloxyethyl)phenoxy]-2-propanol The title compound was prepared by the above method at 50° from betaxalol and α-acetoxyethyl p-nitrophenyl carbonate. IR (film) 3458, 1758, 1712, 1512, 1244, 1681, 1011, 943 cm$^{-1}$. $^1$H NMR (CDCl$_3$) 0.05–0.75 (m, 4H, cyclopropyl CH$_2$), 0.7–1.05 (m, 1H, cyclopropyl CH), 1.21 (d, J=8 Hz, 6H, Me$_{20}$H), 1.5 (d, J=6 Hz, 3H, CH$_3$CH), 2.06 (s, 3H, OAc), 2.81 (t, J=7 Hz, 2H, ArCH$_2$), 3.26 (d, J=7 Hz, 2H, OCH$_2$ cyclopropyl), 3.4–4.4 (m, 9H), 6.81 (q, J=6 Hz, 1H, CH$_3$CH), 6.78 (d, J=10 Hz, 2H, aromatic), 7.08 (d, J=10 Hz, 2H, aromatic). MS, m/e 437 (M+), M+calcd. for C$_{23}$H$_{35}$NO$_7$, 437.2411. obsd. 437.2412.

EXAMPLE 11

N-(Acetoxymethoxycarbonyl)-3-(3',4'-dihydroxyphenyl)-2-methylalanine

The title compound prepared from acetoxymethyl p-nitrophenyl carbonate and benzyl α-amino α-methyl-2,2-diphenyl-1,3-benzodioxole-5-propanoate by the above method, followed by hydrogenolytic deprotection has the following spectral properties: NMR (D$_2$O) 1.40 (s, 3H, CH$_3$), 2.13 (s, 3H, OAc), 3.05 (s, 2H, CH$_2$), 5.63 (s, 2H, OCH$_2$O) and 6.4–6.7 (m, 3H, aromatic). MS, m/e 327 (M+).

EXAMPLE 12

Benzyl N-(acetoxyethoxycarbonyl)-3-(3',4'-dihydroxyphenyl)-2-methylalanine ester A mixture of methyldopa benzyl ester hydrochloride (3.25 g), p-nitrophenyl acetoxyethyl carbonate (2.85 g), 1-hydroxybenzotriazole (1.3 g) and N-methylmorpholine (0.97 g) in hexamethylphosphoramide (15 mL) was stirred at room temperature for 26 hours. The reaction mixture was diluted with 100 mL of water and extracted with ethyl acetate. The organic extract was washed successively with water, 1N HCl, water 2% aqueous Na$_2$CO$_3$ and water. It was then dried over Na$_2$SO$_4$ and evaporated to furnish a residue weighing 2.8 g. Chromatography of this over silica gel impregnated with 5% w/w of KH$_2$PO$_4$ using EtOAc-CHCl$_3$ as eluent furnished 1.66 g of the pure title compound as a foam. IR (KBr) 3410, 2929, 1738, 1609, 1520, 1451, 1236, 1115, 1078, 756 cm$^{-1}$. NMR (CDCL$_3$) 1.3–1.6 (m, 6H, CH$_3$CH and CH$_2$CCH$_3$), 2.05 (s, 3H, acetyl), 2.8–3.6 (m, CH$_2$), 5.13 (s, 2H, C$_6$H$_5$CH$_2$), 6.3–7.0 (m, 3H, aromatic) and 7.26 (s, 5H, aromatic). Exchangeable protons at 5.2 to 5.8; MS, m/e 431 (M+), 327, 254, etc.

EXAMPLE 13

N-(Acetoxyethoxycarbonyl)-3-(3',4'-dihydroxyphenyl)-2-methylalanine

The benzyl ester from example 12 (0.9 g) was dissolved in ethyl acetate (50 mL) and 0.5 mL of acetic acid was added. It was hydrogenated at 40 psi in presence of 0.2 g of 10% Pd on carbon. After 4 hours, the reaction mixture was filtered through celite. The filtrate was evaporated. The residue was triturated three times with hexane. The residue was then redissolved in dry ether. On evaporation of ether it gave a white amorphous hygroscopic powder (0.63 g). IR (KBr) 3412, 2997, 2937, 1732, 1608, 1521, 1451, 1378, 1284, 1251, 1113, 1080, 949 cm$^{-1}$. NMR (D$_2$O) 1.3–1.6 (6H, m, CH$_3$CH and CH$_2$CCH$_3$), 2.08 (s,3H, acetyl), 3.0 (s, 2H, CH$_2$), 6.4–7.0 (m, 4H, aromatic and CH$_3$CH); MS, m/e 341 (M+), 237, 210, 123; High Res. MS, MW calc. for C$_{15}$H$_{19}$NO$_8$, 341.11093; observed, 341.1098.

EXAMPLE 14

Benzyl N-(pivaloxymethoxycarbonyl)-3-(3',4',-dihydroxyphenyl)-2-methylalanine ester Prepared as in example 12 from benzyl methyldopa ester hydrochloride (0.53 g, p-nitrophenyl pivaloxymethyl carbonate (0.37 g), 1-hydroxybenzotriazole (0.17 g), N-methylmorpholine (0.16 g) in hexamethylphosphoramide (5 mL) to give 0.28 g after chromatography. NMR (CDCl$_3$) 1.25 (s, 9H, t-Bu), 1.6 (s, 3H, CH$_3$C), 3.16 (q, 2H, J=14 Hz, CCH$_2$), 5.16 (s, 2H, C$_6$H$_5$), 5.71 (q, 2H, J - 6 Hz, OCH$_2$O), 6.2–6.8 (3H, m, Ar) and 7.33 (5H, C$_6$H$_5$)

EXAMPLE 15

N-(Pivaloxymethoxycarbonyl)-3-(3',4'-dihydroxyphenyl)-2-methylalanine

Prepared as in example 13 by hydrogenalysis of the benzyl ester obtained in example 14. IR (KBr) 3381, 2980, 1736, 1726, 1720, 1604, 1518, 1284, 1063, 1028, 968, 733 cm$^{-1}$;NMR (CDCl$_3$)1.21(s, 9H, t-Bu), 1.58 (s, 3H, CH$_3$C), 3.13 (s, br, 2H, ArCH$_2$), 5.73 (s, 2H, OCH$_2$O), 6.5–6.8 (m, 3H, aromatic) and 7.1 (br, exchangable with D$_2$O). MS, m/e 369 (M+), 238, 207, 192, etc.

EXAMPLE 16

N-(Pivaloxyethoxycarbonyl)-3-(3',4'-dihydroxyphenyl)-2-methylalanine

Was prepared as in examples 14 and 15, but using p-nitrophenyl-pivaloxyethyl carbonate. It has the following spectral properties. IR (KBr) 3385, 2990, 1730 (broad). NMR (CDCl$_3$) 1.20 (s, 9H, t-Bu), 1.56 (s, 3H, CH$_3$C), 1.65 (d, 3H, CH$_3$CH), 3.13 (s, br, 2H, ArCH$_2$), 6.5–7.2 (m, 4H, aromatic and CH$_3$CH) 7.3 (br, exchangable with D$_2$O). MS, m/e 383 (M$^{30}$), 238, etc.

EXAMPLE 17 p-Nitrophenylpalmitoyloxymethyl carbonate

A solution of iodomethyl p-nitrophenyl carbonate in benzene (50 mL) was refluxed with silver palmitate for 1 hour. The reaction mixture was then filtered. The filtrate was washed with 0.5% aqueous sodium hydroxide and water. Evaporation of solvent gave a pale white solid weighing 1.4 g.

EXAMPLE 18

N-(Palmitoyloxymethoxycarbonyl)-3-(3',4'-hydroxyphenyl)-2-methylalanine

A mixture of palmitoylmethyl p-nitrophenyl carbonate (0.45 g), methyldopa benzyl ester hydrochloride (0.45 g), N-methylmorpholine (0.134 g) and 1-hydroxybenzotriazole (0.135 g) in hexamethylphosphoramide (5 mL) were stirred at room temperature for 22 hours. It was then poured into water (50 mL) and extracted with ether-ethyl acetate (1:1). The organic extract was washed successively with water, 1N HCl, water, 1% aqueous Na$_2$CO$_3$ and water. Evaporation of the solvent gave a pale white residue 0.54. Chromatography over silica gel impregnated with 5% w/w of KH$_2$PO$_4$ gave the pure benzyl ester of N-(palmitoyloxymethoxycarbonyl)-3-(3',4'-dihydroxyphenyl)-2-methylalanine (0.35 g). NMR (CDCl$_3$) 0.9 (t, 3H), 1.3 (br, s, 26H), 1.56 (s, 3H), 2.33 (m, 2H), 3.13 (broad s, 2H), 5.13 (s, 2H), 5.66 (q, J=6 Hz, OCH$_2$O), 6.2 to 6.8 (m, 3H), 7.28 (s, aromatic).

Hydrogenalysis of 0.3 g of the above ester in ethyl acetate (25 mL) and acetic acid (1 mL) in presence of 10% Pd-C (0.1 g) at 40 psi for 4 hours gave the pure title compound as a viscous oil.

EXAMPLE 19

N-(Pyridine-3'-carboxymethoxycarbonyl)-3,4-dimethoxyphenethylamine

A solution of dimethoxyphenethylamine (0.4 g) and nicotinyloxymethyl p-nitrophenyl carbonate (0.3 g example 5) in hexamethylphosphoramide (3 mL) was stirred at room temperature for 2 hours. The reaction mixture was diluted with water (30 mL) and extracted with ethyl acetate. The ethyl acetate extract was washed with water, 0.5% cold aqueous sodium hydroxide and water. After drying over $Na_2SO_4$, the extract was evaporated to yield a residue weighing 0.45 g. It was chromatographed on silica gel to furnish 0.39 g of pure title compound on elution with ethyl acetate. NMR ($CDCl_3$) 2.76 (2H, t, J=7 Hz, $ArCH_2$), 3.12–3.66 (2H, m, $NHCH_2$), 3.83 (6H, s, OMe), 5.4 (1H, br t, NH), 5.96 (2H, s, $OCH_2O$), 6.7 (3H, m, aromatic), 7.2–7.5 (1H, m, aromatic), 8.05–8.4 (1H, m, aromatic), 6.7 (1H, dd, J=2 Hz and 7Hz, aromatic) 9.2 (1H, br d, aromatic). IR (film) 3356, 1743, 1739, 1732, 1590, 1517, 1463, 1422, 1267, 1153, 1093, 1020, 960, 742, 701. MS, m/e 360 ($M^+$), 207, 164, 151, 106.

What is claimed is:

1. A compound of the formula:

ps wherein X is phenyl substituted with one or more of the substituents selected from the group consisting of nitro, halo, cyano, $C_{1-6}$ alkylsulfonyl, $C_{1-6}$ alkylsulfenyl, trihalogemthylthio, trihalogemthylsulfonyl, trihalomethylsulfenyl or a radical selected from the group consisting of $C_{1-5}$ polyhaloalkyl and $C_{2-12}$ alkylsulfonylalkyl; $R_1$ is selected from the group consisting of $C_{1-6}$ alkyl, $C_{1-5}$ alkoxycarbonylalkyl, aryl and aralkyl; $R_2$ is selected from the group consisting of hydrogen $C_{1-6}$ alkyl, $C_{1-5}$ alkloxycarbonyl alkyl, aryl and aralkyl; and $R_3$ is selected from the group consisting of $C_{1-20}$ alkyl, $C_{2-20}$ alkenyl, $C_{1-20}$ alkynyl, aryl, $C_{7-10}$ aralkyl, $C_{3-8}$ cycloalkyl, $C_{3-10}$ cycloalkenyl, $C_{2-20}$ carboxyalkyl, carboxy $C_{5-20}$ cycloalkyl, $C_{2-20}$ haloalkyl, $C_{1-5}$ alkoxycarbonyl $C_{2-10}$ alkyl, $C_{2-20}$ alkylsulfoxide, $C_{2-20}$ carbamyl substituted alkyl, $C_{2-20}$ carbamyl substituted aralkyl, and heterocyclics selected from the group consisting of pyridyl, pyrolyl, pyrrolidinyl, and piperidinyl.

2. The compound of claim 1, wherein X is halophenyl, nitrophenyl or polyhaloalkyl; $R_1$ is alkyl, aralkyl, or $C_{1-5}$ alkoxycarbonylalkyl; $R_2$ is hydrogen, alkyl or substituted $C_{1-5}$ alkoxycarbonylalkyl; and $R_3$ is alkyl, aryl, pyridyl or alkoxycarbonylalkyl.

3. The compound of claim 2 wherein X is nitrophenyl, $R_1$ is methyl, $R_2$ is hydrogen and $R_3$ is alkyl.

4. The compound of claim 2, wherein X is nitrophenyl, $R_1$ is benzyl; $R_2$ is hydrogen and $R_3$ is methyl.

5. The compound of claim 2, wherein X is nitrophenyl, $R_1$ is methyl; $R_2$ is hydrogen and $R_3$ is nicotinyl.

6. The compound of claim 2, wherein X is nitrophenyl, $R_1$ is methyl; $R_2$ is hydrogen and $R_3$ is pentyl.

7. The compound of claim 2, wherein X is nitrophenyl, $R_1$ is benzyl; $R_2$ is hydrogen and $R_3$ is t-butyl.

8. The compound of claim 2, wherein X is nitrophenyl, $R_1$ is methyl; $R_2$ is hydrogen and $R_3$ is t-butyl.

9. The compound of claim 2, wherein X is nitrophenyl, $R_1$ is methyl; $R_2$ is hydrogen and $R_3$ is methyl.

10. The compound of claim 2, wherein X is nitrophenyl, $R_1$ is methyl; $R_2$ is hydrogen and $R_3$ is pentadecyl.

* * * * *